United States Patent
Levinson et al.

(10) Patent No.: US 6,352,552 B1
(45) Date of Patent: Mar. 5, 2002

(54) STENT

(75) Inventors: Melvin E. Levinson; George I. Golik, both of Miami, FL (US)

(73) Assignee: Scion Cardio-Vascular, Inc., Miami, FL (US)

( * ) Notice: Subject to any disclaimer, the term of this patent is extended or adjusted under 35 U.S.C. 154(b) by 0 days.

(21) Appl. No.: 09/563,710

(22) Filed: May 2, 2000

(51) Int. Cl.⁷ .................................................. A61F 2/06
(52) U.S. Cl. ..................................................... 623/1.15
(58) Field of Search ................................ 623/1.1, 1.11, 623/1.12, 1.13, 1.14, 1.15, 1.16, 1.17, 1.18, 1.19, 1.2, 1.21, 1.22, 1.23; 606/108, 191, 194, 198, 195

(56) References Cited

U.S. PATENT DOCUMENTS

| | | | |
|---|---|---|---|
| 5,549,663 A | 8/1996 | Cottone, Jr. | 623/1 |
| 5,645,559 A | 7/1997 | Hachtman et al. | 606/198 |
| 5,669,932 A | 9/1997 | Fischell et al. | 606/198 |
| 5,810,872 A | 9/1998 | Kanesaka et al. | 606/198 |
| 6,042,597 A * | 3/2000 | Kveen et al. | 623/1.15 |

OTHER PUBLICATIONS

Coronary Stenting, Current Perspectives; Martin Dunitz Ltd. 1999, London, England (40 pgs in total).

* cited by examiner

Primary Examiner—Henry J Recla
Assistant Examiner—Vy Q. Bui
(74) Attorney, Agent, or Firm—Robert Kain; Fleit, Kain, Gibbons

(57) ABSTRACT

An expandable tubular reinforcing member used for a body lumen that is made from a pair of end sections each constituted of an endless element of sinuous configuration defining a plurality of U-bends, an elongated element of sinuous configuration defining a plurality of U-bends extending between the end sections and spaced therefrom and being disposed in a helical configuration of the same diameter as the end sections. Turns of the helix of the elongate element are spaced apart with the U-bends of the elongated element aligned with the U-bends of the end sections. A plurality of first interconnecting strips, each having a bend, spans the space between axially successive turns of the elongated element and interconnects axially aligned proximate U-bends of the elongated element to define cells bounded by the elongated element and circumferentially successive first interconnecting strips. A plurality of second interconnecting strips, each having a bend, spans the spaces between the elongated element and the pair of end elements and interconnects axially aligned proximate U-bends of the end sections and the elongated element to define cells bounded by the end sections, the elongated element and circumferentially successive second connecting strips.

12 Claims, 1 Drawing Sheet

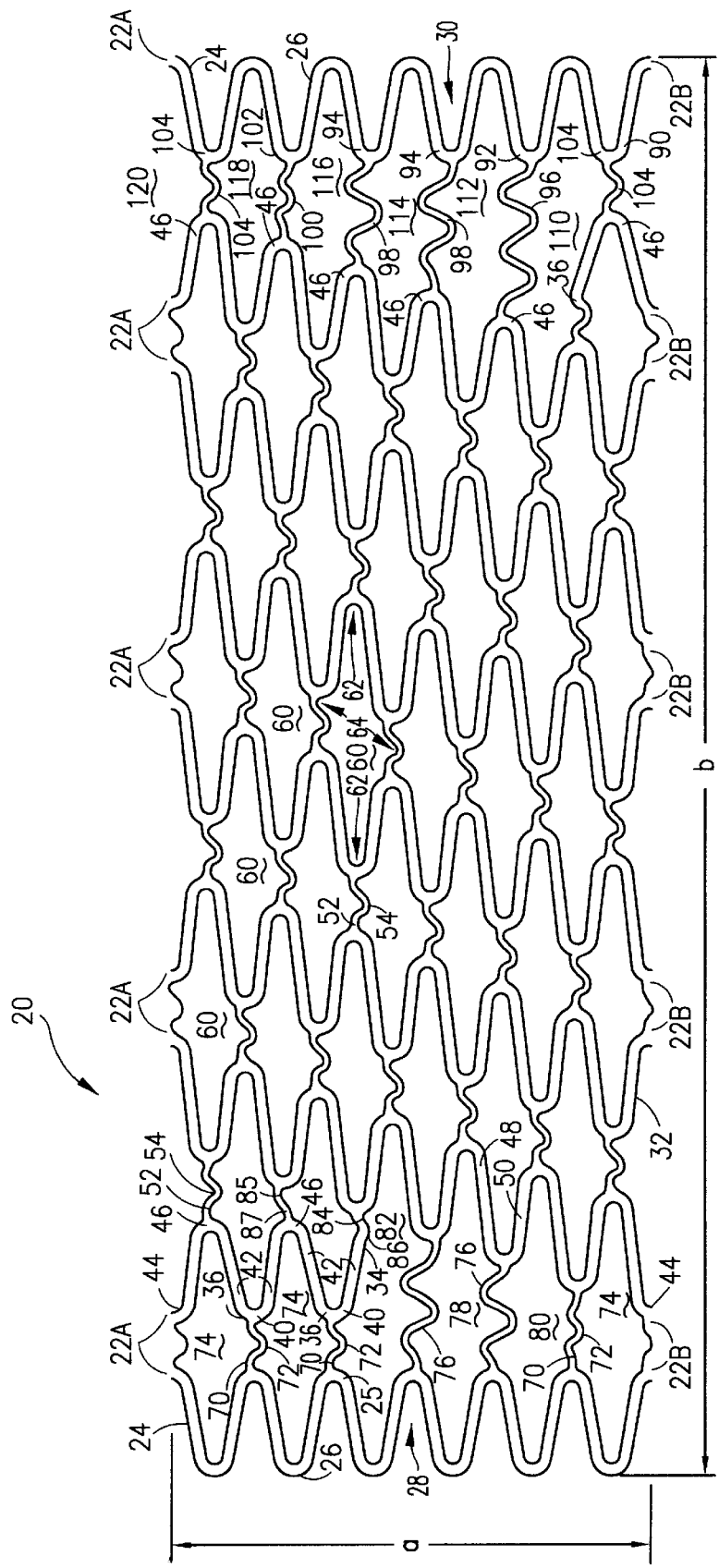

STENT

BACKGROUND OF THE INVENTION

1. Field of the Invention

The present invention relates to an expandable tubular reinforcing member used for a body lumen, such as a blood vessel, for reinforcement, and more particularly to a flexible stent that can be inserted into a body lumen describing a tortuous path and moved to a body cavity where it can be expanded in situ in both the radial and circumferential directions.

2. Description of the Prior Art

The art is quite developed concerning stents for the purpose of reinforcing a weakened body lumen to prevent collapse and occlusion of the fluid passageway defined by the body lumen. As is known, expandable stents are inserted in such body lumens using balloon catheters in a technique known as angioplasty. The stent, usually of tubular cylindrical form, must have an initial diameter that is suitable for insertion through a body lumen and into the targeted body cavity, but must be expandable in the radial and circumferential directions to support a cavity wall to maintain the patency thereof, and the radial strength to support and maintain this capability. Although such stents are in general known, nevertheless, the need for an improved design remains a goal to be sought. The continuing need for a flexible stent, that effectively can be inserted through narrow tortuous passageways of the body into a target body cavity, and which will have the requisite radial strength and support capability in the circumferential direction, still exists.

SUMMARY OF THE INVENTION

Accordingly, it is an object of the present invention to provide a flexible stent that has excellent flexibility to allow it to be inserted into a body lumen and advanced in an axial direction through narrow tortuous passageways, and to have the requisite radial strength and support capability in the circumferential direction to maintain the patency of the body cavity in which it is inserted.

It is a further object of the present invention to provide a flexible stent that is readily expandable by a balloon catheter in radial and circumferential directions.

The foregoing objects of the invention are achieved by a novel design for a stent that employs a unique mesh configuration and cellular construction, and yet is simple to manufacture.

This is accomplished by providing an expandable tubular reinforcing member for use for a body lumen that comprises, a pair of end sections each constituted of an endless expandable element and having a preselected diameter, an elongated element of sinuous configuration defining a plurality of U-bends extending between the end sections and spaced therefrom and being disposed in a helical configuration of said preselected diameter with the turns of the helix being spaced apart, a plurality of first interconnecting strips, each having a bend, spanning the space between axially successive turns of the elongated element and interconnecting axially aligned proximate U-bends of the elongated element to define cells bounded by the elongated element and circumferentially successive first interconnecting strips, and a plurality of second interconnecting strips, each having a bend, spanning the spaces between the elongated element and the pair of end elements and interconnecting the proximate U-bends of the elongated element nearest to the end sections to define cells bounded by the end sections, the elongated element and circumferentially successive second connecting strips.

The U-bends of the elongate element of the expandable tubular reinforcing member have legs that are slightly splayed. Also, for the majority of the elongate element, one leg of the U-bend is longer than the other. However, for at least the first and last U-bends of the elongate element, the legs are of equal length. The expandable tubular reinforcing member has each end section characterized by a sinuous configuration defining a plurality of U-bends which are axially aligned with the proximate U-bends of the elongate element nearest to the end sections. In a preferred design, the expandable tubular reinforcing member is characterized by a pitch of the helix of the elongate element from about 20 to about 25 degrees.

In a more specific form, the expandable tubular reinforcing member used for a body lumen comprises, a pair of end sections each constituted of an endless element of sinuous configuration defining a plurality of U-bends and having a preselected diameter, an elongated element of sinuous configuration defining a plurality of U-bends extending between the end sections and spaced therefrom and being disposed in a helical configuration of said preselected diameter with the turns of the helix being spaced apart, the U-bends of the elongated element being substantially aligned with the U-bends of the end sections, a plurality of first interconnecting strips, each having a bend, spanning the space between axially successive turns of the elongated element and interconnecting axially aligned proximate U-bends of the elongated element to define cells bounded by the elongated element and circumferentially successive first interconnecting strips, and a plurality of second interconnecting strips, each having a bend, spanning the spaces between the elongated element and the pair of end elements and interconnecting axially aligned proximate U-bends of the end sections and the elongated element to define cells bounded by the end sections, the elongated element and circumferentially successive second connecting strips.

In a further development, the strips having bends which divide the cells also serve as common or shared boundaries between a cell and the next preceding cell in the circumferential direction and the next succeeding cell in the circumferential direction. Also, the U-bends of the elongate element act as common or shared boundaries between a cell and the cell next preceding in an axial sense and the cells next succeeding in an axial sense. In the cellular structure developed by the elongate element and the strips, cells in successive turns of the helix are offset by one-half cell in the circumferential direction.

Other and additional advantages and objects of the present invention will become more readily apparent from the following detailed description of a preferred embodiment of the invention when taken with the appended drawing.

BRIEF DESCRIPTION OF THE DRAWING

The sole FIGURE of the drawing shows, in a two dimensional layout, the novel tubular stent of the present invention.

DETAILED DESCRIPTION OF PREFERRED EMBODIMENTS

Referring to the sole FIGURE, there is shown the novel tubular stent of the present invention in a two dimensional layout. As illustrated, the stent 20 is an open mesh or cellular structure, and is shown in its pre-deployed, repose or unexpanded state, as it would appear if it were rolled out into a two dimensional form. It should be understood that the stent 20 is actually in the form of a tubular right cylinder having a central axis both before and after its deployment into a vessel or lumen of the human body. The cylindrical form of the stent 20 may be accomplished by taking the flat form shown in the sole FIGURE and bending or rolling it into a cylinder with all points 22A being joined to all corresponding points 22B. Preferably, however, the stent 20 may be fabricated by laser machining a thin-wall, stainless steel tubular right cylinder, in a manner that will be readily known to one skilled in the art from the following detailed description of a preferred embodiment.

The stent 20 consists of two essential or principal parts or portions and a number of intercoupling or bridging strips of unique design. At each end of the stent 20 is an endless sinuous element 24 with uniform U-bends or loops 26, one set of alternate ones of which lie in a radial plane at the end of stent 20. Another set of alternate ones lie in a radial plane spaced inwardly from the end of stent 20. The U-bends have splayed legs of equal length, and open axially. The U-bends at the end of stent 20 open axially inwardly whereas the U-bends in the radial plane spaced inwardly open axially outwardly. For convenience of description, one end 28 of the stent 20 is referred to as the leading end of stent 20, and the other end 30 of the stent 20 is referred to as the trailing end of stent 20. It will be appreciated however, that in use the ends 28 and 30 of stent 20 are interchangeable and therefore, either end can function as the leading or trailing end.

The other principal part or portion of stent 20 is a continuous sinuous element 32 that starts at point 34 near end 28 and spirals in a helix toward end 30, and terminates at point 36 near end 30. Starting from the leading end 28 and point 34, element 32 makes two U-bends each followed by a reverse U-bend 46, all of which have a characteristic U-bend and have slightly spayed legs 42 of equal length. It will be noted that for convenience of description, U-bends 40 open axially toward the trailing end 30 whereas reverse U-bends 46 open axially toward the leading end 28. Starting with the U-bend 44, which is broken between the top and bottom of the FIGURE, the legs become of different length so that the element 32 begins to spiral toward the trailing end 30. The differential in leg length is such that the pitch of the spiral is from about 20 to about 25 degrees, and the turns of the spiral are spaced apart a short distance. The leg 48 which advances the spiral toward the trailing end 30 is longer than the leg 50 which leads from the leading end 28 of the stent 20 thereby setting the pitch of the spiral.

Interconnecting or coupling the U-bends or loops 40 and the reverse U-bends 46 of the element 32 which lie axially aligned and adjacent to each other, as opposed to the U-bends or loops 40 and the reverse U-bends or loops 46 of the element 32 which lie axially aligned and remote from each other, are strips 52 which are characterized by a U-bend or loop 54 at its mid-point which opens circumferentially in the direction of spiraling or helical movement and which has an amplitude or height that allows for expansion of the coupling length. It will be noted that the strips 52 couple both the U-bends 40 and the reverse U-bends 46 at all locations where the U-bends 40 or reverse U-bends 46 lie in axial proximity. As appears from the sole FIGURE, as the element 32 progresses from point 34 near the leading end 28 toward point 36 near the trailing end 30, turn by turn, the bends 40 and reverse bends 46 appear to lie circumferentially displaced by one bend.

The U-bends 40 and reverse U-bends 46 together with the coupling strips 52 create cells or openings 60 in the stent 20. The cells 60 are roughly of parallelogram or flat diamond shape with opposite long sides 48 and opposite short sides 50. The side axially spaced apexes 62, as shown in the FIGURE, are constituted by one U- bend 40 on the leading side and one axially aligned U-bend 46 on the trailing side. The circumferentially spaced apexes 64, as shown in the sole FIGURE, are constituted by the strips 52. The cells 60 are stacked contiguously in the circumferential spiraling or helical direction, and they spiral from the leading end 28 toward the trailing end 30 where they terminate at point 36. The cells 60 also are contiguous in the axial direction albeit axially contiguous cells 60 are displaced circumferentially by one-half cell.

The leading end or edge of the spiraling or helical element 32 is coupled to the end element 24 by means of strips 70 which are like strips 52 in that they are characterized by a mid-bend 72, and open in the same circumferential sense. There are four such strips 70, and they interconnect the reverse U-bends 25 on the trailing side of element 24 with the corresponding axially aligned U-bends 40 on the leading side of the element 32. This creates three cells 74. There are two strips 76, longer than the strips 70 and having a sinuous configuration with a larger mid-bend that extends for 540 degrees (one and one half sinusoidal waves). Each strip 76 interconnects a reverse U-bend 25 on the trailing side of element 24 with the corresponding axially aligned U-bend 40 on the leading side of element 32. This creates a cell 78. The length of the strips 76 is necessitated by the spiral of element 32. There is one cell 80 created between a strip 70 and strip 76, and a second larger cell 82 created between the other strip 76 and strip 70 and the beginning leg of element 32 at point 34 and a further strip 84 which is about one-half the length of a strip 70, but includes a bend 86. This is necessitated because at this axial alignment, the element 32 is at its furthest departure from the leading end 28 before it starts to turn on itself in its spiral. Also, the first cell 59 defined by element 32 is bounded by a U-bend 40 with equal legs, a U-bend 40 with unequal legs, a strip 85 with bend 87 and the first strip 52.

At the trailing end 30, the element 24 is coupled or interconnected to the spiral or helical element 32, in generally the same way, with the following modifications. There is only one final reverse U-bend 46 with legs of equal length, which is interconnected with the axially aligned U-bend 90 on element 24. (See the lower, right portion of the sole FIGURE). Interconnecting U-bends 92 and 94 of element 24 with the substantially axially aligned reverse U-bends 46 of element 32 are one strip 96 and two strips 98. Strip 96 is of sinuous configuration and extends for 720 degrees, and each strip 98 is of sinuous configuration and extends for 540 degrees, like strips 76. A strip 100 interconnects U-bend 102 of element 24 with axially aligned U-bend 46 of element 32 and is slightly longer than strips 70 which interconnect the reverse U-bends 46 of element 32 with the axially aligned U-bends 104 of the element 24. The bends 92 and 94 are not exactly axially aligned with the reverse U-bends with which they are connected, but they are only slightly circumferentially displaced. The displacement, however is only slight and they approximate axial alignment.

The trailing end of stent 20 defines the following special cells. Cell 110 is bounded by elements 32 and 24 and strips 96 and 104. Cell 112 is bounded by elements 32 and 24 and strips 96 and 98. Cell 114 is bounded by elements 32 and 24 and strips 98. Cell 116 is bounded by elements 32 and 24 and strips 98 and 100. Cell 118 is bounded by elements 32 and 24 and strips 100 and 104. Cell 120, which is divided top and bottom, is bounded by elements 32 and 24 and strips 104. The variation in the interconnections between the reverse U-bends of element 32 and the U-bends of element 24 and their lengths are necessitated by the variation in axial distance resulting from the spiral or helix of element 32.

In a specific preferred dimensional embodiment, the circumference a of the stent is 0.2152 inches, the axial length b of the stent is 0.6609 inches, as shown on the FIGURE, the splay of the legs of the U-bends of element is about 0.017 inches and the radius of the U-bends is about 0.0085 inches.

As previously noted, the stent 20 is positioned on a balloon catheter and inserted into a body lumen to a cavity location in the body where it is to be expanded (radially about its axial centerline) to hold the walls of the cavity in a supported state to prevent closure of the cavity and maintain fluid flow patency. The stent 20 of the present invention will expand readily under the influence of the balloon catheter, and will maintain its expanded state with appropriate force and resistance to counter-forces which are asserted on the expanded stent due to the tissues constituting the walls of the body cavity in which it is located. During expansion of stent 20, it will diminish in axial length and increase in radius or diameter and circumference. The generally parallelogram or flat diamond configuration of the cells acting in combination with the U-bends in the interconnecting strips facilitate the expansion and provide the requisite rigidity for maintaining its expanded configuration.

Typically, the stent is made of stainless steel but other biocompatible materials may be utilized. Stress tests on the stent described herein reveal that maximum axial shrinkage or foreshortening in the center cell of the stent is about 16%. When placed under full expansion, very little relative cellular rotation observed. Peak stains are located in the radii of the U-bends.

Although the invention has been shown and described in terms of specific embodiments, nevertheless changes and modifications will be apparent to those skilled in the art from the teachings herein. Such changes and modifications are deemed to fall within the purview of the invention as herein claimed.

What is claimed is:

1. An expandable tubular reinforcing member used for a body lumen comprising,
   (a) a pair of end sections each constituted of an endless expandable element and having a preselected diameter,
   (b) an elongated element of sinuous configuration defining a plurality of U-bends extending between the end sections and spaced therefrom and being disposed in a helical configuration of said preselected diameter with the turns of the helix being spaced apart,
   (c) a plurality of first interconnecting strips, each having a bend, spanning the space between axially successive turns of the elongated element and interconnecting axially aligned proximate U-bends of the elongated element to define cells bounded by the elongated element and circumferentially successive first interconnecting strips, and
   (d) a plurality of second interconnecting strips, each having a bend, spanning the spaces between the elongated element and the pair of end elements and interconnecting the proximate U-bends of the elongated element nearest to the end sections to define cells bounded by the end sections, the elongated element and circumferentially successive second connecting strips.

2. The expandable tubular reinforcing member of claim 1 wherein the U-bends of the elongated element have legs that are slightly splayed.

3. The expandable tubular reinforcing member of claim 2 wherein one leg of the U-bend is longer than the other.

4. The expandable tubular reinforcing member of claim 2 wherein at least the first and last U-bends of the elongate element have legs of equal length.

5. The expandable tubular reinforcing member of claim 1 wherein each end section is of a sinuous configuration defining a plurality of U-bends which are axially aligned with the proximate U-bends of the elongate element nearest to the end sections.

6. The expandable tubular reinforcing member of claim 1 wherein the pitch of the helix of the elongate element is from about 20 to about 25 degrees.

7. An expandable tubular reinforcing member used for a body lumen comprising,
   (a) a pair of end sections each constituted of an endless element of sinuous configuration defining a plurality of U-bends and having a preselected diameter,
   (b) an elongated element of sinuous configuration defining a plurality of U-bends extending between the end sections and spaced therefrom and being disposed in a helical configuration of said preselected diameter with the turns of the helix being spaced apart, the U-bends of the elongated element being substantially aligned with the U-bends of the end sections,
   (c) a plurality of first interconnecting strips, each having a bend, spanning the space between axially successive turns of the elongated element and interconnecting axially aligned proximate U-bends of the elongated element to define cells bounded by the elongated element and circumferentially successive first interconnecting strips, and
   (d) a plurality of second interconnecting strips, each having a bend, spanning the spaces between the elongated element and the pair of end elements and interconnecting axially aligned proximate U-bends of the end sections and the elongated element to define cells bounded by the end sections, the elongated element and circumferentially successive second connecting strips.

8. The expandable tubular reinforcing member of claim 7 wherein the U-bends of the elongate element have legs that are slightly splayed.

9. The expandable tubular reinforcing member of claim 8 wherein one leg of the U-bend is longer than the other.

10. The expandable tubular reinforcing member of claim 8 wherein at least the first and last U-bends of the elongate element have legs of equal length.

11. The expandable tubular reinforcing member of claim 7 wherein each end section is of a sinuous configuration defining a plurality of U-bends which are axially aligned with the proximate U-bends of the elongate element nearest to the end sections.

12. The expandable tubular reinforcing member of claim 7 wherein the pitch of the helix of the elongate element is from about 20 to about 25 degrees.

* * * * *